United States Patent [19]

Hotta

[11] 4,264,820
[45] Apr. 28, 1981

[54] METHOD AND APPARATUS FOR MAKING X-RAY PHOTOGRAPHS OF JAW STRUCTURE

[75] Inventor: Mitsuhiko Hotta, Kyoto, Japan

[73] Assignee: Kabushiki Kaisha Morita Seisakusho, Kyoto, Japan

[21] Appl. No.: 952,099

[22] Filed: Oct. 17, 1978

[30] Foreign Application Priority Data

Oct. 31, 1977 [JP] Japan .................................. 52-131076

[51] Int. Cl.³ ....................... G01N 21/00; G01N 23/00
[52] U.S. Cl. ................................................. 250/439 P
[58] Field of Search ....................................... 250/439 P

[56] References Cited

U.S. PATENT DOCUMENTS

| | | | |
|---|---|---|---|
| 3,536,913 | 10/1970 | Huchel | 250/439 P |
| 3,806,731 | 4/1974 | Kataoka et al. | 250/439 P |
| 4,145,611 | 3/1979 | Valila | 250/439 P |

Primary Examiner—Alfred E. Smith
Assistant Examiner—Thomas P. O'Hare
Attorney, Agent, or Firm—Koda and Androlia

[57] ABSTRACT

A method of apparatus for making X-ray photographs of a jaw structure which makes it possible to obtain clear and distinct images of the dental arch without superimposition of neighboring teeth and further to equalize the enlargement ratio of images to be made on the film no matter which spots of the teeth may be taken at the time of X-ray photographing.

8 Claims, 9 Drawing Figures

METHOD AND APPARATUS FOR MAKING X-RAY PHOTOGRAPHS OF JAW STRUCTURE

BACKGROUND OF THE INVENTION

1. Field of the Invention

This invention is related to a method and an apparatus for making X-ray photographs of a whole jaw structure for dental use.

2. Prior Art

As generally known, X-ray photographic units of this type are developed by using the tomographic technology to adapt curved planes so that the whole jaw structure can be closely examined. Those photographs for dental use have, of course, to be very clear to the teeth.

However, the conventional units are not free from some mechanical defects. For example, in the case of a three-circle-composite elliptic arc, an X-ray photograph is taken by succeedingly shifting the camera along its locus from the first locus to the second and further to the third locus. This process requires the camera to move about three different centers of gyration, which makes the driving mechanism very complex and the pictures unclear particularly around those spots where the camera is moved into a different locus. The Applicant has invented a radiographic apparatus as described in the Japanese Application No. 53,165/72 which overcomes the defect mentioned above. The principal structure of this apparatus is such that the crossing paths intersecting at right angle to each other are provided on a fixed base with sliders which are movable in their own path, while an arm spanned between the sliders gets to swing to create an elliptical locus.

Thus, the X-ray film holder disposed on one end of the arm is induced to shift continuously and smoothly analogous to the dental arch of the subject. This apparatus can produce clear and distinct pictures because there is no necessity for changing the center of gyration as explained above. However, this apparatus is not free from some problems such as occurrence of the superimposition of images of neighboring teeth due to the fact that the X-ray beam is projected in a little oblique direction to an individual tooth, especially in its adjacent region; and also there remained unsolved another question as to the difference in the enlargement ratio between images made on the film of each one of the teeth or even between both ends of one single tooth. In consideration of the above, a new radiography apparatus as in the Japanese Patent Application No. 97,303/74 (Laid Open Patent No. 24,889/76) was developed. In this apparatus, a circular arc path and a straight-line path passing through the center thereof were formed on the base, and sliders shifting in these two paths, respectively, were provided in place of such sliders shifting in the directions intersecting each other at right angles alike in the above apparatus, thereby the X-ray film holder on the arm end being allowed to move continuously and smoothly analogous to the dental arch of the subject. In this apparatus, the X-ray beam is projected in the direction substantially intersecting at right angles to an individual tooth of the dental arch, especially to the adjacent region of them, so that it became possible to eliminate at least the defect of the superimposition of teeth neighboring each other. Nevertheless, remained unsolved the problem of the difference in the enlargement ratio between images made on the film of an individual tooth or even between both ends of one single tooth.

SUMMARY OF THE INVENTION

This invention has as its object to provide a new X-ray photographing method to solve the defects involved in the existing prior art method and also to provide a novel apparatus for producing dental X-ray photographs of the whole jaw structure to be used in such method.

Description will be now directed to the X-ray photographing method according to the invention with reference to the accompanying drawings.

DETAILED DESCRIPTION OF THE INVENTION

Figure 1:
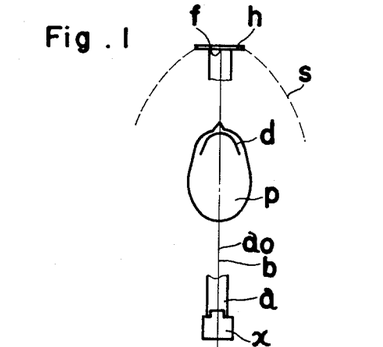
FIG. 1 illustrates an operational diagram showing an embodiment of the method of this invention.

The method used in the present invention is a method of making X-ray photographs of the whole jaw structure for dental use. The general concept of this invention is as shown in FIG. 1, in which an X-ray generator (hereinafter referred to as X-ray source) x and an X-ray film holder h are mounted on opposite sides of an arm a in such a manner as to face each other with reference to the axis $a_o$ of the arm a while keeping the relative position to each other invariable. The film holder h here is made to shift along a chain line S analogous to a dental arch d of a subject p, while maintaining the predetermined correlation between itself and the X-ray source x, at the same time when the focusing X-ray beam b from the X-ray source x is urged to be radiated continuously upon the face of the film f contained in the X-ray film holder h. Thus, it becomes possible to make tomographs of curved planes in the dental arch d. Such is the photographing method which adapts the principles illustrated in FIGS. 2 and 3 or 6.

Figure 2:
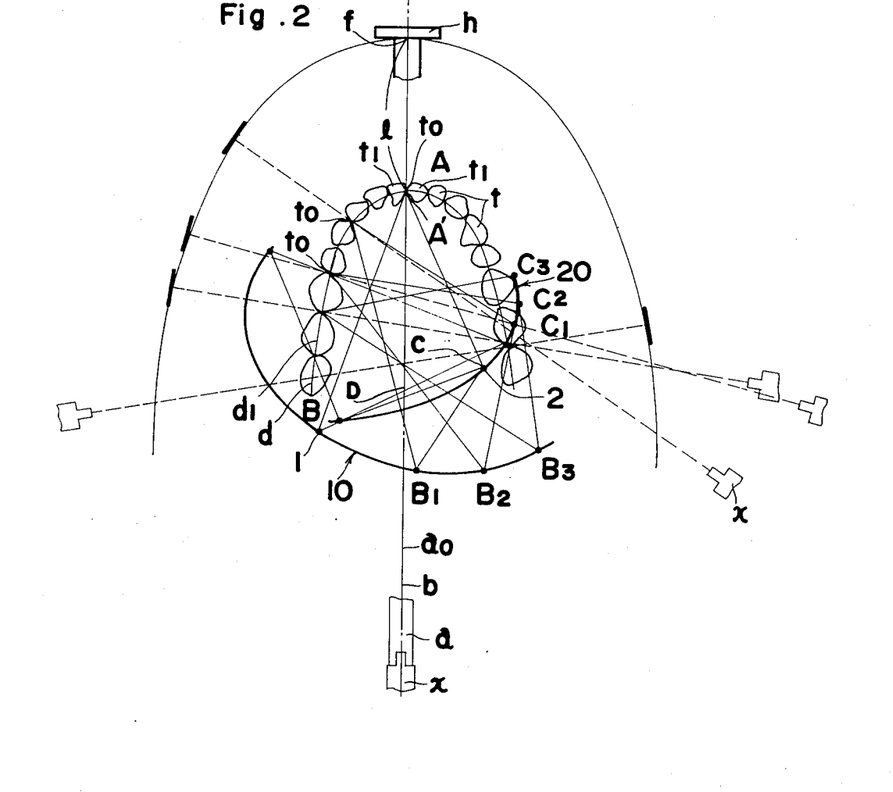
FIGS. 2 and 3 illustrates an enlarged operational diagram shown in FIG. 1.
Figure 3:
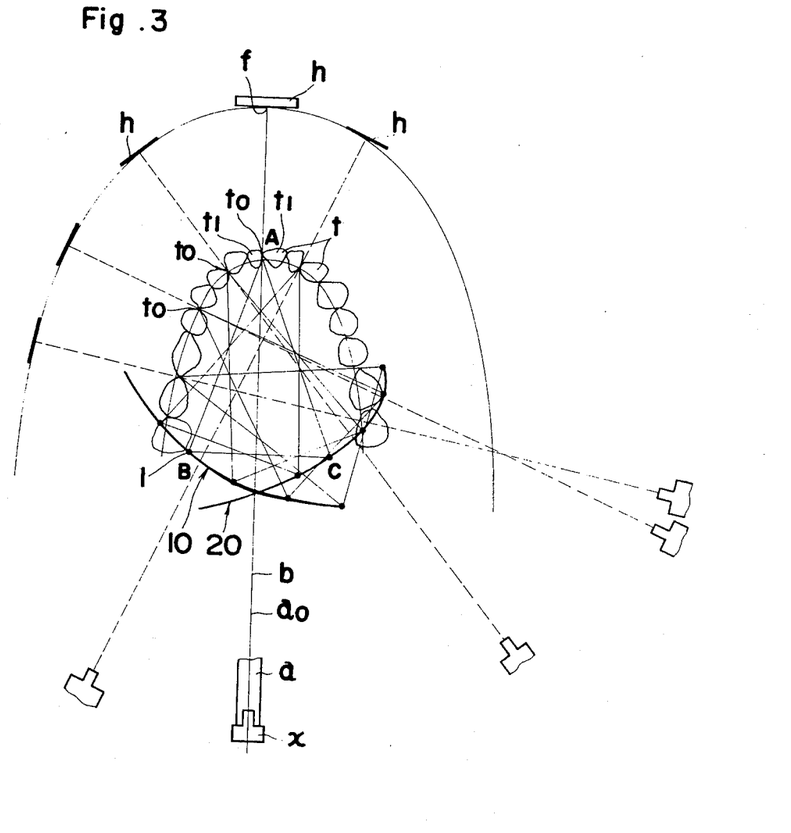

The method based on the principles in FIGS. 2 and 3 is a method of making X-ray photographs of the whole jaw structure for dental use, which is characterized in such a construction as follows:

Collaterally to the arm a between the film holder h and the X-ray source x, not less than two driving points for swinging 1 and 2 are provided separately in the positions which lie apart from the axis $a_o$ of the arm a and keep the immovable relation to the arm a. Then, to these driving points, swinging 1 and 2, are imparted curvilinear motions 10 and 20 independent of each other. Through the cooperative regulation of these two curvilinear motions 10 and 20, the arm a is made to swing within the area of a plane containing the axis $a_o$ of the arm a whereby the X-ray beam b comes to be projected in the direction substantially intersecting at right angles, as a minimum, to any given neighboring point $t_o$ of each individual tooth t in the dental arch d, and whereby the film f to be exposed to the X-ray beam b is able to shift analogous to the dental arch d in the substantially equidistant relation to any tooth t in the dental arch d. (In this connection, another photographing method which adapts the principle illustrated in FIG. 6 will be described hereinafter.)

Figure 4:
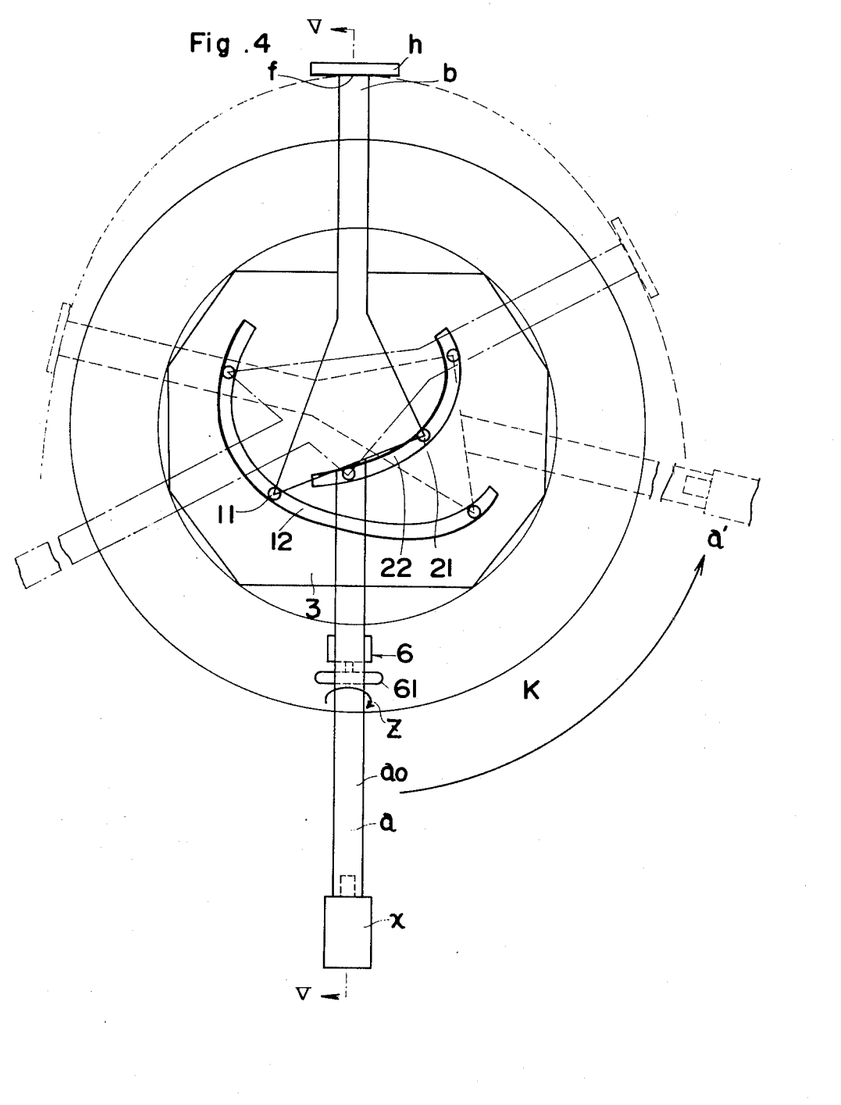
FIG. 4 illustrates a top plan view of an embodiment of the apparatus according to the invention.
Figure 5:
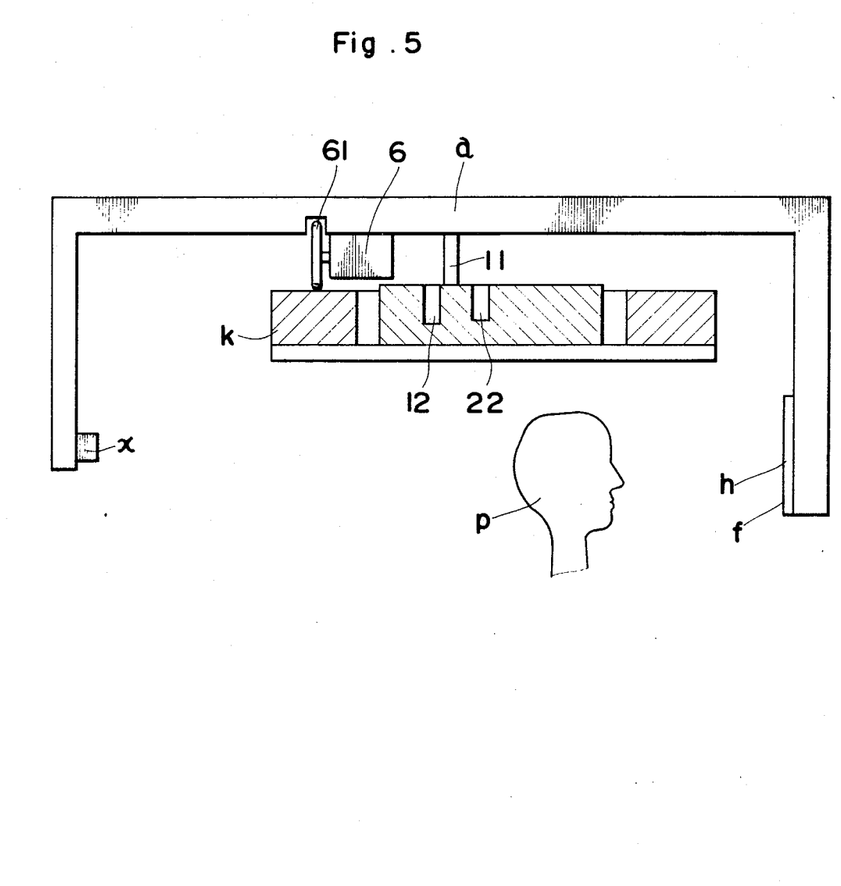
FIG. 5 illustrates a cross-sectional view taken along the line V—V of FIG. 4.

As an example of the apparatus used in the above-mentioned method can be taken the one illustrated in FIGS. 4 and 5. In summary, the dental apparatus of making X-ray photographs of the whole jaw structure illustrated here comprises an X-ray source x and an X-ray film holder h both being mounted on opposite sides of an arm a in such a manner as to face each other relatively to the axis $a_o$ of said arm while keeping the relative position to each other invariable; swing sliders 11 and 21 being provided in the immovable relation to the arm a at least each on either side across the axis $a_o$ of the arm a midway between the X-ray source x and the X-ray film holder h; curvilinear guide paths 12 and 22 being provided on a base 3 independently of each other in order to guide the respective sliders 11 and 21; and a driving power source 6 being provided on the arm a; wherein the arm a is brought about to swing through the cooperative regulation of the sliders 11 and 21 which are guided in the curvilinear guide paths 12 and 22, in company with which the film holder h is made to shift analogous to the dental arch d of the subject p and on the other hand, the focusing beam b from the X-ray source x comes to incide in the direction substantially intersecting at right angles to any given neighboring point $t_o$ of an individual tooth t in the dental arch d, while the face of the films f in the holder h to be exposed to the X-ray beam b is induced to move in the substantially equidistant relation to any tooth in the dental arch d.

The apparatus in this illustration is the one that adapts the principle and method illustrated in FIG. 2, as mentioned above. The swing sliders 11 and 21 (shown in FIG. 4) of this apparatus are provided correspondingly to the respective vertexes B and C of the triangle ABC in FIG. 2. The reason for this is that it is necessary for this photographing method to have at least two driving points 1 and 2 for swinging in positions which are apart from the arm a and keep the fixed relation to the arm a. These driving points 1 and 2 for swinging are determined as follows: At the middle (median) point A' between the first two incisors is one vertex A of an arbitrary triangle ABC, the other vertexes B and C are set up in any position on either side across the axis $a_o$ and these two vertexes B and C are each driving points 1 and 2 for swinging. A line is drawn from the vertex A to the point D at which the line B–C intersects the axis $a_o$ of the arm a, that is, the line A–D is congruent with the axis therewith $a_o$ of the arm a, and further, this axis $a_o$ is also congruent with the X-ray beam b; therefore, the line A–D is congruent with the X-ray beam b. Now when the point A on the line A–C shifts along the standard dental line $d_1$ of the dental arch d, the triangle ABC is forced to shift in such a way that the line A–D shall always be substantially normal to the standard dental line $d_1$ at any given neighboring point $t_o$ of an individual tooth t and as shown in FIG. 2, the points B and C each shift successively tracing one after another the points $B_1$, $B_2$, $B_3$ . . . or $C_1$, $C_2$, $C_3$ . . . with the shifting movement of the point A. If these shifting points $B_1$, $B_2$ . . . or $C_1$, $C_2$ . . . are connected in succession, curved lines as indicated by the reference numerals 10 and 20 are generated. These curved lines are equivalent to the moving locus of the above-mentioned curvilinear motions 10 and 20 independent of each other, respectively. It is apparent from the above that the curvilinear guide paths 12 and 22 in the above illustrated apparatus are motion guides for putting the above curvilinear motions 10 and 20 into operation. In this example, the X-ray film holder h and the X-ray source x of the apparatus are provided on the extension line of the line A–D of the triangle ABC, wherein the enlargement ratio of images depends on the length l from the vertex A of the triangle ABC to the face of the film f in the film holder h. As for the swing sliders 11 and 21 (shown in FIG. 4) of the apparatus in this example, they are provided each on either side across the axis $a_o$ of the arm a. However, the number of sliders 11 and 21 (shown in FIG. 4) is not necessarily limited to only two pieces as in this case. It is permissible of course to place a plurality of sliders at any appropriate position together with an equal number guide paths associated with the respective sliders. For the same reason, the curvilinear guide paths 12 and 22 are also restricted in number only to two such as illustrated in the example and also the form of the curvilinear guide paths 12 and 22 (shown in FIG. 4) can vary endlessly depending on the arbitrary setting of the vertexes B and C of the triangle ABC. For example, the points B and C in FIG. 2 which forms a foundation also for the apparatus of FIGS. 4 and 5, are positioned asymetrically each on either side across the axis $a_o$ of the arm a and lie along the axis $a_o$ of the arm a in sliding relation to each other; therefore, their motion loci take a form of the reference numerals 10 and 20 in FIG. 2. In another modification illustrated in FIG. 3, however, curvilinear motions 10 and 20 of the same form intersect each other, unlike the curvilinear motions 10 and 20 in FIG. 2, when the points B and C are located in a symmetrical relation each on either side across the axis $a_o$ of the arm a. That is, since the curvilinear guide paths are formed in accordance with curvilinear motions 10 and 20 of the points B and C, it is natural that the form of the guide paths 12 and 22 varies depending on the respective curvilinear motions 10 and 20 of the points B and C. It may be said in this connection that if the points B and C are placed too close to the axis $a_o$, the smoothness of the swinging movement of the arm a will be expected. For this reason, it is desirable to set up the relation of the points B and C to the axis $a_o$ of the arm a neither too close nor too far away within the scope of preventing the apparatus from growing too large. Incidentally, though the swing sliders 11 and 21 are positioned within the area of the same plane with each other in the illustration, they can be also placed on different planes separately above and below and the curvilinear guide paths 8 and 9 each may be provided within their own planes.

Description will be now directed to the gist of the operation and effects of the hitherto-mentioned apparatus with reference to FIGS. 4 and 5. By way of example, when the roller 6 rotates in the direction of the arrow Z over the sliding platform k, the arm a swings in the direction of the arrow a' while the swing sliders 11 and 21 fixed on the arm a on either side across the axis $a_o$ of the arm a shift while being regulated by the respective curvilinear guide paths 12 and 22. At this time, the curvilinear guide paths 12 and 22 is nothing less than the forms of the shifting loci of the points B and C of the triangle ABC, the line A-C of which is made to shift so as to become substantially the normal line to the standard dental line $d_1$ at all times, as mentioned above. This means that the line A-C conforms with the direction of the X-ray beam b. Therefore, the X-ray beam b always incides intersecting substantially at right angles to the standard dental line $d_1$, to be more precise, to any given neighboring point of individual teeth t, in consequence of which the superimposition of neighboring teeth can be avoided as far as possible. As for the enlargement ratio (value) of images, it depends on the length l from the vertex A of the triangle ABC up to the face of the film f in the film holder h, as described before. But the length l has been specified to be always constant from the beginning, so that the face of the film f comes to keep a certain distance from individual teeth t while shifting continuously analogous to the dental arch d. As a result, the stable enlargement ratio of images recorded on the film can be obtained maintaining a substantially equal value for any tooth t. And what is better, it is possible with this apparatus to acquire clear and distinct images without any distortion, on account of the fact that the swing sliders 11 and 21 which are provided apart from the arm a and maintain the immovable relation thereto, are placed in a position to shift continuously and smoothly in the curvilinear guide paths 12 and 22.

Figure 6:
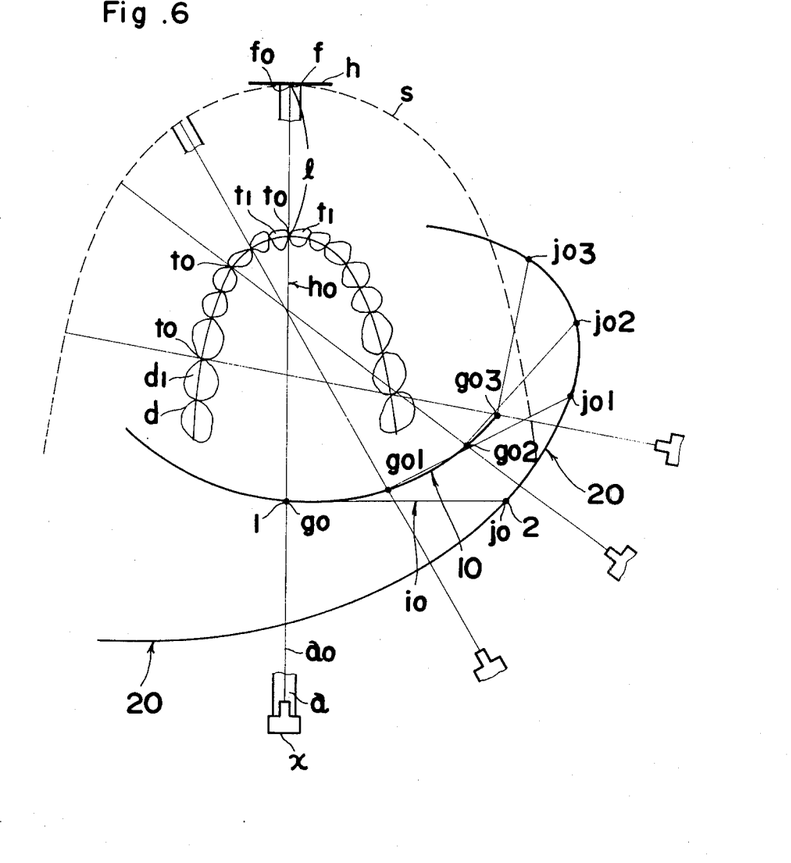
FIG. 6 illustrates another embodiment of the method of this invention.

The different point of the principle and method adapted in FIG. 6 from those in the hitherto described embodiment lies in that out of two driving arms a, while the other two are positioned apart from the axis $a_o$ of the arm a, but in the immovable relation to the arm a. In other words, contrary to the previous embodiment in which both of driving points 1 and 2 are provided each apart from the axis $a_o$ of the arm a and in the immovable relation thereto, the difference of the principle and method in FIG. 6 from it resides in the provision of one out of two driving points on the very axis $a_o$ of the arm a. This photographing method is such a one of X-ray photographing the whole jaw structure for dental use wherein the arm a is caused to swing within the area of the plane containing the axis $a_o$ of the arm a itself by the cooperative regulation of the two curvilinear motions 10 and 20 independent of each other and different in form from each other which are imparted separately to the driving point 1 for swinging positioned on the axis $a_o$ of the arm a and to the driving point 2 for swinging provided apart from the axis $a_o$ of the arm a and in the immovable relation to the arm a, thereby the X-ray beam b coming to be projected substantially intersecting at right angles at least to any given neighboring point $t_o$ of individual teeth t, and further thereby the face of the film f exposed to the X-ray beam b being able to shift in the substantially equidistant relation to any tooth t.

Figure 7:
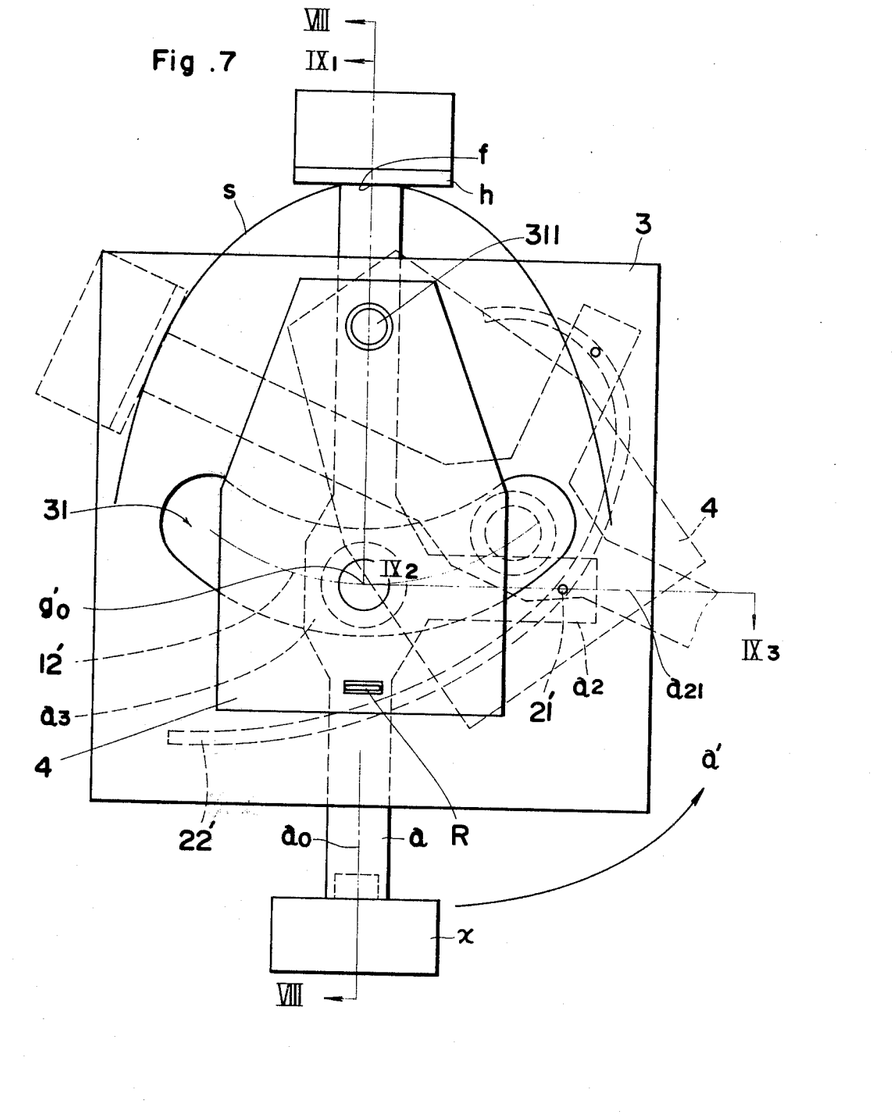
FIG. 7 illustrates a top plan view of another embodiment of the apparatus according to the invention.
Figure 8:
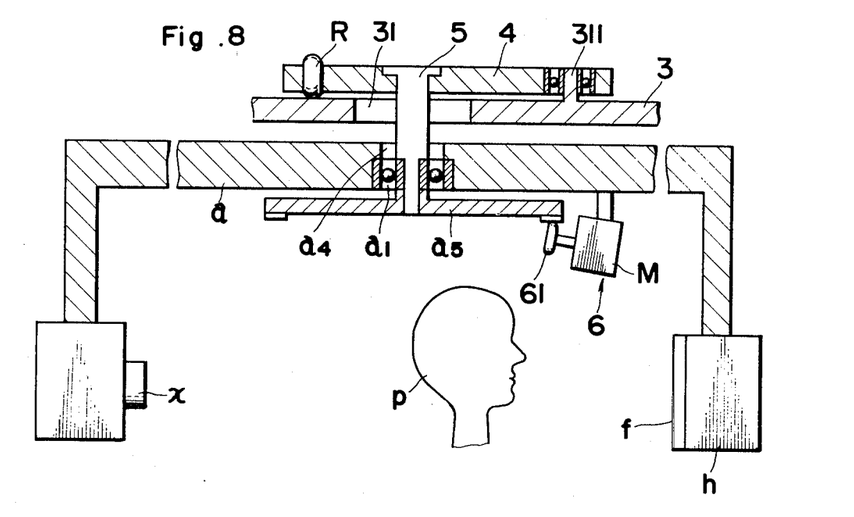
FIG. 8 illustrates sectional view taken along the line VIII—VIII in FIG. 7.
Figure 9:
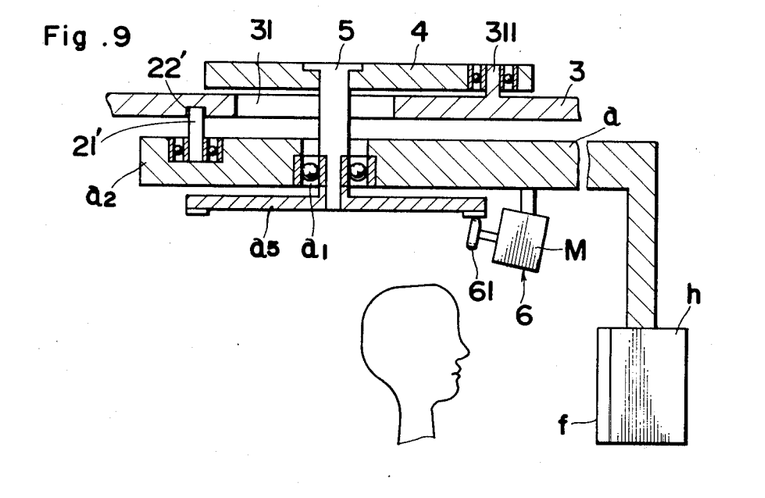
FIG. 9 illustrates sectional view taken along the line $IX_1$-$IX_2$-$IX_3$ in FIG. 7.

The apparatus used in this method is such a type as shown in FIGS. 7, 8 and 9, namely, a dental apparatus of making X-ray source x and an X-ray film holder h being mounted on opposite sides of an arm a in such a manner as to face each other with reference to the axis $a_o$ of the arm a while keeping the relative position to each other invariable; a shaft bearing $a_1$ being attached to the arm a; not less than a branch arm $a_2$ being provided projecting in the different direction from the axis $a_o$ of the arm a and in the immovable relation to the arm a; a swing slider 21 being provided on the branch arm $a_2$; a base 3 being fixed above the arm a to suspend the arm a and having a borehole 31 in the middle part; a rotating plate 4 being provided on the base 3 to swing freely with a point of it 3 as a rotor shaft 311; a connecting means 5 connecting the rotating plate 4 to the arm a in the above-and-below relation and floatingly passing through the borehole 31; a driving power source 6 for swinging being equipped on the underside of the arm a; and a curvilinear guide path 22' being provided on the bottom of the base 3 or between the base 3 and the arm a to guide the swing slider 21'; wherein the arm a is put into swing through the driving power source 6 while being regulated by the swing slider 21' in the curvilinear guide path 22' so as to induce the film holder h to shift analogously to the dental arch d of the subject p, thereby the focusing X-ray beam b from the X-ray source x coming to incide intersecting substantially at right angles successively to any given neighboring point of individual teeth t in the dental arch d, and further thereby the face exposed to the X-ray beam b of the film f in the film holder h being able to shift in the substantially equidistant relation to any tooth t in the dental arch d.

The apparatus in this embodiment is the one which adapts the principle and method illustrated in FIG. 6, as mentioned above, wherein first is drawn the normal line $h_o$ passing through the neighboring point $t_o$ of the first two central incisors $t_1$ and $t_1$ in the dental arch d. This normal line $h_o$ is to be congruent with the axis $a_o$ of the arm a and also the X-ray beam b. On the normal line $h_o$ is taken an arbitrary point $f_o$ at a distance outside the point of contact $t_o$ of the incisors t and t. This arbitrary point $f_o$ serves as the seat of the face of the film f. And also at a distance inside the point of contact is taken on the normal line $h_o$ another arbitrary point $g_o$. Now the neighboring point $t_o$ on the normal line $h_o$ is forced to shift along the dental arch line $d_1$ so as to become substantially the normal line $h_o$ to any given neighboring point $t_o$ of individual teeth t on the dental arch line $d_1$ each time of the shifting movement of the neighboring point $t_o$. Then another arbitrary point $g_o$ shifts as $g_o1$, $g_o2$, $g_o3$ . . . in the Figure to give a translating curvilinear motion 10. On the other hand, a fixed line $i_o$ is drawn from the point $g_o$ rectangularly to the normal line $h_o$, and an arbitrary point $j_o$ is taken on the fixed line $i_o$. If the point $j_o$ is caused to translate as $j_o1$, $j_o2$, $j_o3$ . . . in the Figure, another translating curvilinear motion 20 will be given with the shifting movement of the normal life $h_o$.

The form of the curvilinear guide path 22 of the apparatus in the above-described example has been designed so as to fit exactly to the curvilinear motion 20 which was given by the aforesaid principle. The shaft bearing $a_1$ in this apparatus is a type of radial bearing, which is to be placed in a hole $a_4$ bored in an enlarged part $a_3$ which is stretching from the arm a. In this embodiment, branch arm $a_2$ is projecting in the rectangular direction to the axis $a_1$ of the arm a and that in the immovable relation to the arm a. On the axis $a_{21}$ of this branch arm $a_2$ is provided a swing slider 21. The base 3 is provided above the arm a fixedly on the wall or ceiling of the room or else with the use of some suitable means. The borehole 31 provided nearly in the middle part of the base 3 is formed with the object of not obstructing shifting movement of the connecting means 5 which is provided to shift in proportion as the point of intersection $g_o$ of the axis $a_o$ of the arm a intersecting the axis $a_{21}$ of the branch arm $a_2$ and the axis $a_o$ of the arm a a driving point for swinging. In this embodiment, on the position where a driving point for swinging is expected to be formed, however, is not provided a slider, but exists only an imaginary curvilinear guide path 12' for swinging. This is for the purpose of aiming at the more smoothly swinging of the arm a. Accordingly, it may be said that the borehole 31 functions here similarly to a curvilinear guide path. The rotating plate 4 is for suspending the arm a practically. The base 3 is provided fixedly. The connecting means shifting within the borehole 31 provided in the base 3. In such an arrangement, the rotating plate 4 is designed to rotate with the rotor shaft 311 as a fulcrum within a sectoral sphere. It is for this reason that the connecting means 5 is made to pass through the borehole 31 floatingly. In the capacity of the connecting means 5 is employed in this illustration a bolt. The aforesaid driving power source 6 for swinging comprises of a motor M and a roller 61. The sliding platform $a_5$ for the roller 61 is provided immovably below the radial bearing $a_1$ on the front end of the connecting means 5.

In this connection, the above-mentioned branch arm $a_2$ is not limited to be provided projecting only in the direction intersecting at right angles to the arm a. There is also no limitation in the number of it; not only one piece but also plural ones may be set so far as they are provided in the immovable relation, not to speak of the possibility of providing at will so many corresponding guide paths independently. The guide path 22' in the illustration is embedded directly in the under face of the base 3, but a similar guide groove can be bored in plate body fixed horizontally between the base 3 and arm a (not shown). The reference letters R in FIGS. 7 and 8 indicate a roller for swinging.

With the foregoing in mind, reference will be now directed to the main point of operation and its working effect of the apparatus in the above-mentioned second example. As seen in FIGS. 7 and 8, when the arm a is urged to swing in the direction of the arrow a' by dint of the driving power source 6, the face of the film f in the X-ray film holder h shifts describing such a locus as S in FIG. 7, as a result of the slider 21' on the branch arm $a_2$ being regulated by the curvilinear guide path 22'. This shifting locus is the one that is thoroughly congruent with the shifting locus described by the arbitrary point $f_o$ on the normal line derived from the principle illustrated in the previously explained FIG. 6. In FIG. 6, the length 1 between the neighboring point $t_o$ and the arbitrary point $f_o$ both lying on the normal line at any given time is always definite and unchangeable, so that the face of the film f shifts analogous to the dental arch d while keeping the substantially equidistant relation to any given tooth t in the dental arch d. On the other hand, since the form of the curvilinear guide path 22' in this apparatus has been determined substantially on the basis of the normal line $h_o$ passing through each of the neighboring points $t_o$ of an individual tooth t, it is evident for everybody that the axis $a_o$ of the arm a which swings being regulated by the above-mentioned curvilinear guide path 22', that is, the very X-ray beam b comes to incide intersecting substantially at right angles to any given neighboring point $t_o$ of individual teeth t. Hence, like the case of the apparatus in the first example, in the apparatus in this second example, also, it is made possible to obtain clear and distinct images having a constant and stable enlargement ratio without any superimposition. Into the bargain, not more than a single slider will do in this apparatus, as a result leading to the guarantee of the more smooth swinging movement of the arm a.

As understood clearly from the above-mentioned, the method and apparatus according to the invention may be said to be an excellent one which has succeeded in solving at a stroke the controversial points hitherto in question.

Having described our invention as related to the embodiment shown in the accompanying drawings, it is our intention that the invention be not limited by any of the details of description, unless otherwise specified, but rather be construed broadly within its spirit and scope as set out in the accompanying claims.

I claim:

1. A method of making X-ray photographs of a jaw structure for dental use, which comprises the steps of:
    mounting an X-ray source x and an X-ray film holder h on opposite sides of an arm in such a manner as to face each other with reference to an axis $a_o$ of said arm a;
    inducing said X-ray film holder h to shift relative to a dental arch d of a subject p while keeping the relative position between said X-ray source x and said X-ray film holder h invariable;
    radiating a focusing X-ray beam b from said X-ray source x continuously to the face of a not yet exposed film f in said X-ray film holder h in order to make tomographs of curved planes of said dental arch d; and
    causing two driving points of said arm provided midway between said film holder and source to swing through two independent curvilinear paths at the same time while inducing said film holder to shift relative to said dental arch whereby said X-ray beam from said source always intersects said dental arch at substantially right angles to said dental arch and the X-ray film to which the X-ray beam is irradiated can move with a constant distance at any position from the teeth of the dental arch.

2. A method as set forth in claim 1, wherein the respective curvilinear motion of said two driving points are executed both within the same plane parallel to the plane containing the axis $a_o$ of the arm a.

3. A method as set forth in claim 1, wherein the respective curvilinear motions of said two driving points are executed separately in two planes different from each other both parallel to the plane containing the axis $a_o$ of the arm a.

4. A method as set forth in any of claims 1, 2 and 3, wherein any curvilinear motions are executed by the sliding movement of respective sliders provided at said driving points.

5. A method as set forth in claim 1, wherein the two driving points for swinging are placed asymmetrically and separately respectively across and along the axis $a_o$ of the arm a.

6. A method as set forth in claim 5, wherein the two driving points for swinging are placed symmetrically left and right across the axis $a_o$ of the arm a.

7. A dental apparatus for X-ray photographing of a jaw structure, which comprises: an X-ray source x and an X-ray film holder h being mounted on opposite ends of an arm a in such a manner as to face each other with reference to an axis $a_o$ of said arm a while keeping the relative position to each other invariable; swing sliders being provided midway between said X-ray source x and said X-ray film holder h at least each on either side of said arm a and in immovable relation to said arm a; two curvilinear guide paths being provided independently of each other on a base for guiding the respective sliders; and a driving power source being provided on said arm a in order to force said arm a to swing relatively to said base; whereby said arm a is put into swinging movement by virtue of cooperative regulation of the respective curvilinear motions of said sliders which are being guided in said curvilinear guide paths, said film holder h shifts relative to a dental arch d of the subject p, a focusing X-ray beam b from said X-ray source x intersects substantially at right angles to any given neighboring point $t_o$ of individual teeth t in the dental arch and a face of a film f in said film holder h which is to be exposed to said X-ray beam b shifts in substantially equidistant relation to any tooth t in a dental arch d.

8. A dental apparatus for X-ray photographing a jaw structure, which comprises: an X-ray source x and an X-ray film holder h being mounted on opposite sides of an arm a in such a manner as to face each other with reference to an axis $a_o$ of said arm a while keeping the relative position to each other invariable; a shaft bearing $a_1$ being attached to said arm a; not less than one branch arm $a_2$ being provided projecting in a different direction from the axis $a_0$ of said arm a and in immovable relation to said arm a; a swing slider being provided on said branch arm $a_2$; a base being fixed above said arm a for suspending said arm and being provided with a bore hole in a middle part thereof; a rotating plate being provided over said base to swing freely with a point thereon as a fulcrum; a connecting means being floatingly passed through said borehole while cojoining said rotating plate and said arm a in an above and below relation; a driving power source for swinging being attached to said arm a; and a curvilinear guide path being provided on a bottom of said base whereby said arm a is put into swinging movement with the aid of said driving power source while being regulated by said slider in said curvilinear guide path, said film holder h shifts relative to a dental arch d of the subject p, a focusing X-ray beam b from said X-ray source x intersects substantially at right angles to any given neighboring point $t_0$ of an individual tooth t in a dental arch d, and the face of a film f in said film holder h which is to be exposed to said X-ray beam b shifts in a substantially equidistant relation to any tooth t in a dental arch d.

* * * * *